US00PP19750P2

(12) United States Plant Patent
Cain et al.

(10) Patent No.: US PP19,750 P2
(45) Date of Patent: Feb. 17, 2009

(54) GRAPEVINE PLANT NAMED 'SUGRATHIRTYFOUR'

(50) Latin Name: *Vitis vinifera*
Varietal Denomination: Sugrathirtyfour

(75) Inventors: David W. Cain, Bakersfield, CA (US); Michael J. Striem, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 12/004,258

(22) Filed: Dec. 19, 2007

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

PP10,434 P 6/1998 Cain
PP13,164 P2 11/2002 Cain

*Primary Examiner*—Annette H Para
(74) *Attorney, Agent, or Firm*—Knobbe, Martens, Olson & Bear LLP

(57) ABSTRACT

A new and distinct grapevine variety characterized by producing dark-red skinned, very juicy, firm, round berries that have an excellent eating quality. The berries ripen late season, having a naturally large size and high sugar content.

1 Drawing Sheet

Latin name of the genus and species claimed: *Vitis vinifera.*
Variety denomination: 'Sugrathirtyfour'.

BACKGROUND AND SUMMARY OF THE INVENTION

This invention relates to the discovery and asexual propagation of a new and distinct variety of grapevine as herein described and illustrated. The new variety was first hybridized by David Cain in Wasco, Kern County, Calif., the variety being originated by controlled hybridization and subsequent culture of seed traces and embryo rescue procedures.

The new variety 'Sugrathirtyfour' is characterized by producing late ripening, dark-red skinned grapes. The berries have a naturally large size, a round shape, high sugar content, and excellent eating quality. 'Sugrathirtyfour' is exceptional with its dark-red almost black color development when ripening. The new variety 'Sugrathirtyfour' ripens at the end of the season, about three months after 'Sugrathirteen' (U.S. Plant Pat. No. 10,434), about ten days or two weeks after 'Autumn Royal' (unpatented), and about three weeks after 'Sugratwentythree' (U.S. Plant Pat. No. 13,164).

The seed parent is the varietal selection '91171-094-492' (unpatented) and the pollen parent is the varietal selection '92167-052-375' (U.S. Plant Pat. No. 13,164), otherwise known as 'Sugratwentythree'. The parent varieties were first crossed in May 1999, by David Cain. From the initial population of hybrid ovules, embryo rescue methods were used to produce a population from which the present variety was selected. The date of first sowing was August 1999, and the date of first flowering was May 2003.

The new variety 'Sugrathirtyfour' was first asexually propagated in December 2003, in Wasco, Kern County, Calif., by Michael J. Striem using hardwood cuttings.

The new variety 'Sugrathirtyfour' resembles its seed parent '91171-094-492' in many characteristics, such as the same dark-red (almost black) color type with the same type of cluster structure, but differs from its seed parent in that it is not as brittle and the bunch is not as loose as its parent. Additionally, 'Sugrathirtyfour' does not develop noticeable seed-traces as its parent would.

The new variety 'Sugrathirtyfour' resembles its pollen parent '92167-052-375' or Sugratwentythree in many characteristics, such as the same dark-red (almost black) color type with the same type of cluster structure. Additionally, similar to its pollen parent, 'Sugrathirtyfour' has strong pedicles and peduncle resulting in a good attachment of the berries, the skin of the fruit is similar in thickness, but is not tannin and astringent as the skin of 'Sugratwentythree.' The new variety 'Sugrathirtyfour' also differs from its pollen parent '92167-052-375' in that the berries of the pollen parent are elliptical and much smaller (6.5 gr.) whereas those of the new variety 'Sugrathirtyfour' are round and larger (9.1 gr.). Additionally, 'Sugrathirtyfour' ripens approximately 3 weeks after the pollen parent.

The new variety 'Sugrathirtyfour' resembles the comparable variety 'Sugrathirteen' in its color and neutral flavor. However, 'Sugrathirtyfour' ripens at the end of the season, three months after Sugrathirteen. The berries of 'Sugrathirtyfour' are rounder and naturally much larger (9.1 gr. vs. 4.71 gr.).

The new variety 'Sugrathirtyfour' differs from the comparable variety 'Autumn Royal' in that 'Sugrathirtyfour' has a much larger berry size (9.1 gr. vs. 6.3 gr.) and ripens later by about 10 days or two weeks. In addition the berries of 'Sugrathirtyfour' are firmer and have almost no seed trace, while those of 'Autumn Royal' may bear a significantly detectible, dark and hard seed trace.

The new 'Sugrathirtyfour' variety has been shown to maintain its distinguishing characteristics through successive asexual propagations by, for example, cuttings.

Variations of the usual magnitude from the described above may occur with changes in growing conditions, irrigation, fertilization, pruning, management and climatic variations.

BRIEF DESCRIPTION OF THE FIGURE

The accompanying drawing in FIG. 1 illustrates in full color a typical cluster of berries, a young shoot, and a mature leaf blade of the new grapevine. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England.

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrathirtyfour' plants grown in the vicinity of Wasco, Kern County, Calif., during 2006 and 2007, and is believed to apply to plants of the variety grown under similar conditions of soil and climate elsewhere.

VINE

General:

*Planting.*—Trained to a modified gable trellis, planted in a 7 ft.×12 ft. spacing.

*Practices.*—Gene-pool-vine: Cane pruned to approximately 6 canes per vine, 6–8 buds per cane, and trimmed once in the early summer. Test-vines: Cane pruned to approximately 12 to approximately 18 two-bud-spurs per vine, and tested also as cane pruned to approximately 6 canes per vine, 6–8 buds per cane.

*Size.*—Medium. Height: Approximately 2.0 m. Width: Approximately 2.2 m.

*Vigor.*—Vigorous.

*Fresh pruning weight.*—Approximately 1.78 kg per vine.

*Density of foliage.*—Dense.

*Productivity.*—Medium productivity — approximately 20 clusters per vine.

*Yield.*—Approximately 14 kg per vine, thinned to approximately 20 clusters per vine.

*Crop load.*—Approximately 14 kg per vine (kg fruit per kg fresh-pruning-weight).

*Root stock.*—Not applicable.

*Own root.*—Yes.

Trunk:

*Shape.*—Circular.

*Diameter.*—Approximately 64 mm.

*Straps.*—Short.

*Surface texture.*—Shaggy.

*Inner bark color.*—Near Dark Grey Orange 165A.

*Outer bark color.*—Near Grey 201A.

SHOOTS

Young shoot:

*Form of tip.*—Half open.

*Distribution of anthocyanin coloration of tip.*—Absent.

*Intensity of anthocyanin coloration of tip.*—Absent.

*Density of prostrate hairs on tip.*—Absent.

*Density of erect hairs on tip.*—Absent.

Woody shoot (mature canes):

*Shape.*—Slender.

*Internode length.*—Approximately 71.5 mm.

*Width at node.*—Approximately 10.4 mm.

*Cross section.*—Circular.

*Surface.*—Smooth.

*Main color.*—Light Grey Orange 166A+C.

*Lenticels.*—Absent.

*Density of erect hairs on nodes.*—Absent.

*Density of erect hairs on internodes.*—Absent.

*Growth of auxiliary shoots.*—Medium.

Flowering shoot:

*Attitude during flowering on shoots which are not tied.*—Semi-erect.

*Color of dorsal side of internodes.*—Near Medium Yellow Green 144A.

*Color of ventral side of internodes.*—Near Medium Yellow Green 144B.

*Color of dorsal side of nodes.*—Near Medium Yellow Green 144B.

*Color of ventral side of nodes.*—Near Medium Yellow Green 144B.

*Density of erect hairs on nodes.*—Absent.

*Erect hairs on internode.*—Absent.

*Density of prostrate hairs on nodes.*—Absent.

*Density of prostrate hairs on internodes.*—Absent.

*Anthocyanin coloration of buds.*—Absent.

Tendrils:

*Distribution on the shoot at full flowering.*—Discontinuous.

*Thickness.*—Thin.

*Color.*—Near Light Yellow Green 145A.

*Form.*—Bifurcated.

*Number of consecutive tendrils.*—Up to 2.

*Length of tendril.*—Medium, approximately 17 cm.

LEAVES

Young leaves:

*Color of upper surface of first 4 distal unfolded leaves.*—Near green.

*Average intensity of anthocyanin coloration of six distal leaves prior to flowering.*—Absent.

*Density of prostrate hairs between veins at lower surface of 4th distal unfolded leaf.*—Absent.

*Density of erect hairs between veins at lower surface of 4th distal unfolded leaf.*—Absent.

*Density of prostrate hairs on veins at lower surface of 4th distal unfolded leaf.*—Absent.

*Density of erect hairs on veins at lower surface of 4th distal unfolded leaf.*—Absent.

Mature leaves:

*Average length.*—Approximately 127 mm.

*Average width.*—Approximately 170 mm.

*Size of blade.*—Medium.

*Shape of blade.*—Circular.

*Number of lobes.*—Approximately 5.

*Anthocyanin coloration of main veins on the upper side of the blade.*—Absent.

*Mature leaf profile.*—Flat.

*Blistering surface of blade upper surface.*—Very Weak.

*Leaf blade tip.*—In the plane of the leaf.

*Undulation of margin.*—Slight.
*Thickness.*—Medium.
*Undulation of blade between main and lateral veins.*—Absent.
*Shape of teeth.*—Mixture of both straight and convex on both sides.
*Length of teeth.*—Long.
*Ratio length/width of teeth.*—Large.
*General shape of petiole sinus.*—Wide open.
*Tooth at petiole sinus.*—Absent.
*Petiole sinus limited by veins.*—Absent.
*Shape of upper lateral sinus.*—Closed.
*Depth of upper lateral sinus.*—Shallow.
*Density of prostrate hairs between veins on lower surface of blade.*—Absent.
*Density of erect hairs between veins on lower surface of blade.*—Absent.
*Density of prostrate hairs on main veins on lower surface of blade.*—Absent.
*Density of erect hairs on main veins on lower surface of blade.*—Absent.
*Density of prostrate hairs on main veins on upper surface of blade.*—Absent.
*Autumn coloration of leaves.*—Near Grey Purple, 183A–187A.

Upper surface:
*Color.*—Near Dark Yellow Green 147A.
*Surface texture.*—Smooth.
*Surface appearance.*—Dull.

Lower surface:
*Color.*—Near Dark Yellow Green 147B.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:
*Length of petiole.*—Long, approximately 9.5 cm.
*Length of petiole compared to middle vein.*—Slightly longer.
*Diameter.*—Approximately 3 mm.
*Density of prostrate hairs on petiole.*—Absent.
*Density of erect hairs on petiole.*—Absent.
*Shape of base of petiole sinus.*—V-shaped.
*Color.*—Stripes of Yellow Green 144A+Grey Purple 183C.

Buds:
*Shape.*—Conical.
*Size.*—Medium, approximately 5 mm×5 mm.
*Position.*—Slightly held out.
*Cane bud fruitfulness.*—Basal most fruitful.
*Time of bud burst.*—Late.

FLOWERS

General:
*Flower sex.*—Hermaphrodite.
*Length of first inflorescence.*—Medium, approximately 17 cm.
*Position of first flowering node.*—Fifth node.
*Number of inflorescences per shoot.*—1.1 to 2.
*Date of full bloom.*—Mid-May.
*Time of bloom.*—Late.
*Size (diameter of fully open flower).*—Medium, approximately 5 mm.

FRUIT

General:
*Ripening period.*—Late, approximately three months after 'Sugrathirteen' (U.S. Plant Pat. No. 10,434) and approximately three weeks after 'Sugratwentythree' (U.S. Plant Pat. No. 13,164).
*Use.*—Table grapes.
*Keeping quality.*—Good.
*Shipping quality.*—Good.
*Date of first harvest.*—First week of September.
*Solids-sugar.*—High (≈20%).
*Refractometer test.*—Approximately 20.0.
*Acid.*—High, approximately 4.76 gr./L tartaric acid.
*Juice pH.*—Approximately 4.0.
*Resistance.*—Neither resistance nor susceptibility to diseases or pests has been observed in this variety.

Cluster:
*Bunch size (peduncle excluded).*—Medium.
*Bunch length (peduncle excluded).*—Medium, approximately 21.5 cm.
*Bunch width.*—Approximately 12.6 cm.
*Bunch weight.*—Medium, approximately 572 g.
*Bunch density.*—Medium.
*Number of berries.*—Approximately 62.
*Form.*—Conical.

Peduncle:
*Length of peduncle.*—Medium, approximately 12.6 mm.
*Lignification of peduncle.*—Medium.
*Color.*—Near Medium Yellow Green 144A.

Berry:
*Size.*—Large.
*Uniformity of size.*—Variable.
*Berry weight.*—Heavy, approximately 9.1 gr.
*Shape.*—Round.
*Presence of seeds.*—Rudimentary.
*Cross section.*—Circular.
*Dimensions.*—Longitudinal axis: Approximately 24.5 mm. Horizontal axis: Approximately 21.6 mm.
*Skin color (without bloom).*—Near Dark-Red almost Black 202A.
*Juiciness of flesh.*—Very juicy.
*Berry firmness.*—Firm.
*Particular flavor.*—None.
*Bloom (cuticular wax).*—Weak.
*Pedicel length.*—Medium, approximately 8.5 mm.
*Berry separation from pedicel.*—Medium.
*Visibility of hilum.*—Slightly.

Skin:
*Thickness.*—Thin.
*Texture.*—Medium.
*Reticulation.*—Absent.
*Roughness.*—Absent.
*Tenacity.*—Tenacious to flesh.

Seed:
*Number of seeds per berry.*—Approximately 0.8.
*Size.*—Small.
*Color.*—Green.
*Texture.*—Soft.
*Endosperm.*—Absent.
*Fresh weight of seed-traces/berry.*—Approximately 0.96 mg.
*Room-dry weight of seed-traces/berry.*—Approximately 0.90 mg.

What is claimed is:

1. A new and distinct variety of grapevine as herein illustrated and described.

* * * * *

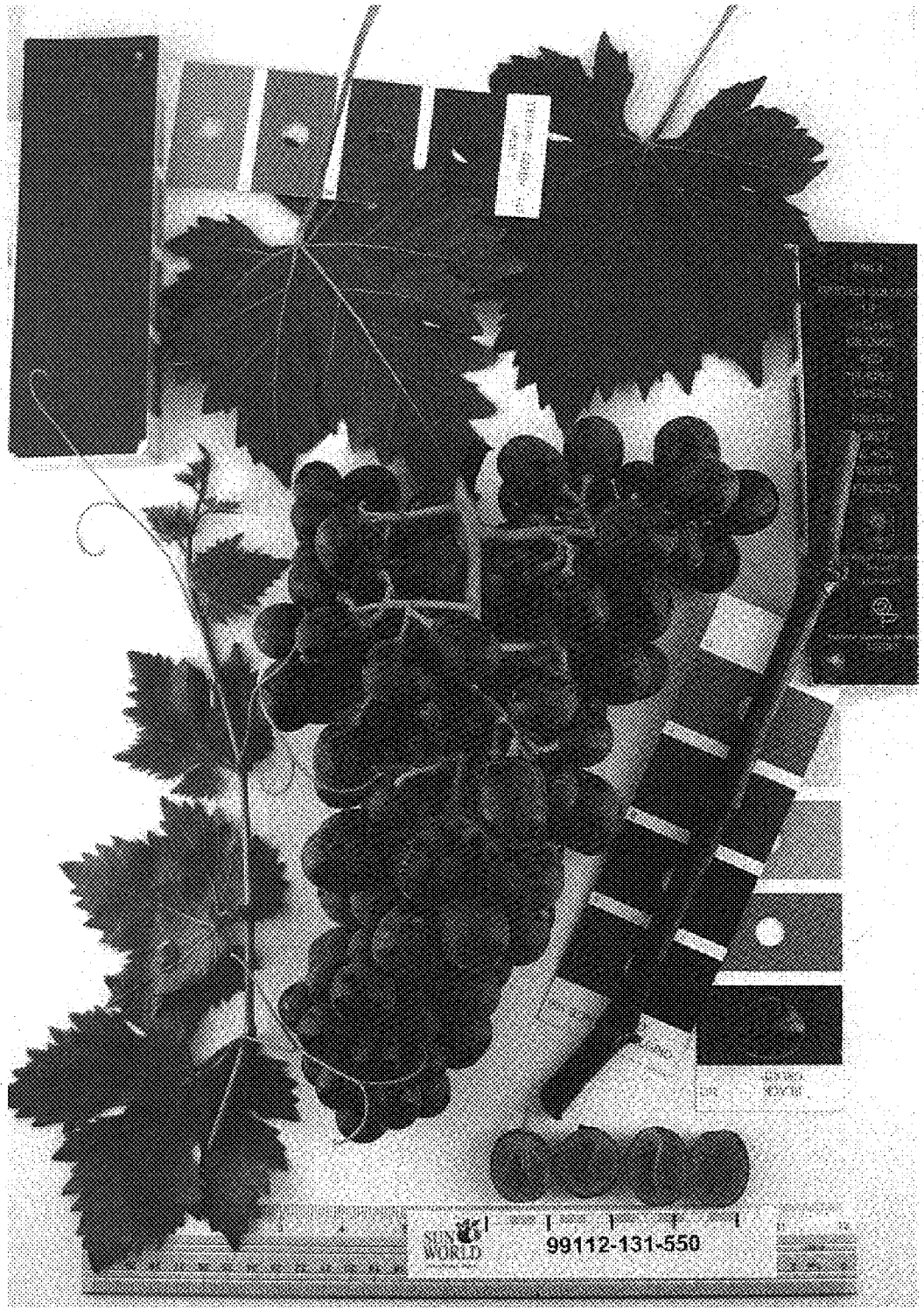
SUN WORLD
99112-131-550